(12) United States Patent
Irisawa et al.

(10) Patent No.: US 11,412,935 B2
(45) Date of Patent: Aug. 16, 2022

(54) PHOTOACOUSTIC MEASUREMENT APPARATUS

(71) Applicant: FUJIFILM Corporation, Tokyo (JP)

(72) Inventors: Kaku Irisawa, Kanagawa (JP); Dai Murakoshi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 642 days.

(21) Appl. No.: 16/128,845

(22) Filed: Sep. 12, 2018

(65) Prior Publication Data

US 2019/0008393 A1  Jan. 10, 2019

Related U.S. Application Data

(63) Continuation of application No. PCT/JP2017/012513, filed on Mar. 28, 2017.

(30) Foreign Application Priority Data

Mar. 29, 2016 (JP) .............................. JP2016-066025

(51) Int. Cl.
*A61B 5/00* (2006.01)
*A61B 8/13* (2006.01)
(Continued)

(52) U.S. Cl.
CPC .......... *A61B 5/0095* (2013.01); *A61B 5/6848* (2013.01); *A61B 5/7225* (2013.01);
(Continued)

(58) Field of Classification Search
CPC ... A61B 5/0095; A61B 5/6848; A61B 5/7225; A61B 8/13; A61B 8/42; A61B 8/463;
(Continued)

(56) References Cited

U.S. PATENT DOCUMENTS

| 5,729,012 A | * | 3/1998 | Wood | ...................... | F42B 3/113 |
| | | | | | 250/226 |
| 2001/0001260 A1 | * | 5/2001 | Parker | .................. | G02B 6/0008 |
| | | | | | 362/572 |

(Continued)

FOREIGN PATENT DOCUMENTS

| JP | 2011-120795 A | 6/2011 |
| JP | 2013-192857 A | 9/2013 |

(Continued)

OTHER PUBLICATIONS

International Preliminary Report on Patentability and Written Opinion of the International Searching Authority(Forms PCT/IB/326, PCT/IB/373 and PCT/ISA/237), dated Oct. 11, 2018, for International Application No. PCT/JP2017/012513, with an English Translation of the Written Opinion.

(Continued)

*Primary Examiner* — Amanda Lauritzen Moher
*Assistant Examiner* — Brooke Lyn Klein
(74) *Attorney, Agent, or Firm* — Birch, Stewart, Kolasch & Birch, LLP

(57) ABSTRACT

A photoacoustic measurement apparatus includes: a main light source; a sub-light source; a light guide member that guides the light which has been emitted from the main light source and the sub-light source and has been incident on a base end to a leading end; an insert of which at least a leading end portion is inserted into a subject and which includes at least the leading end of the light guide member and a light absorption member that absorbs the pulsed laser light, and generates photoacoustic waves; and a photoacoustic wave detection unit that detects the photoacoustic waves. The photoacoustic measurement apparatus has, as an operation mode, a failure detection mode that drives the sub-light source and detects a failure of a photoacoustic wave gen- (Continued)

eration unit including the light guide member and the light absorption member.

22 Claims, 8 Drawing Sheets

(51) Int. Cl.
*A61B 8/00* (2006.01)
*A61B 8/08* (2006.01)
*A61M 5/32* (2006.01)
*A61B 17/34* (2006.01)
*A61B 5/145* (2006.01)
*H04Q 1/22* (2006.01)

(52) U.S. Cl.
CPC .................. *A61B 8/13* (2013.01); *A61B 8/42* (2013.01); *A61B 8/463* (2013.01); *A61B 8/5246* (2013.01); *A61B 17/3403* (2013.01); *A61M 5/32* (2013.01); *A61B 5/14503* (2013.01); *A61B 5/7405* (2013.01); *A61B 2017/3413* (2013.01); *A61B 2562/0257* (2013.01); *H04Q 1/22* (2013.01)

(58) Field of Classification Search
CPC .............. A61B 8/5246; A61B 17/3403; A61B 6/14503; A61B 2017/3413; A61B 2572/0257; A61M 5/32; H04Q 1/22
See application file for complete search history.

(56) References Cited

U.S. PATENT DOCUMENTS

| | | | | |
|---|---|---|---|---|
| 2004/0210112 | A1* | 10/2004 | Ota | A61B 1/0684 600/180 |
| 2007/0147033 | A1* | 6/2007 | Ogawa | A61B 1/0669 362/230 |
| 2007/0149858 | A1* | 6/2007 | Ogawa | A61B 1/0669 600/181 |
| 2009/0086193 | A1* | 4/2009 | Aoki | G01M 11/3127 356/73.1 |
| 2011/0245616 | A1* | 10/2011 | Kobayashi | A61B 1/0653 600/178 |
| 2013/0031982 | A1 | 2/2013 | Sato et al. | |
| 2014/0005556 | A1* | 1/2014 | Hirota | A61B 5/0095 600/476 |
| 2014/0316239 | A1* | 10/2014 | Kasamatsu | H01S 3/121 600/407 |
| 2015/0297092 | A1 | 10/2015 | Irisawa | |
| 2016/0058278 | A1* | 3/2016 | Smith | A61B 3/0008 351/221 |

FOREIGN PATENT DOCUMENTS

| | | | |
|---|---|---|---|
| JP | 2015-37519 A | 2/2015 | |
| WO | WO-2014109148 A1 * | 7/2014 | ............... A61B 8/12 |

OTHER PUBLICATIONS

International Search Report(Form PCT/ISA/210), dated Jul. 25, 2017, for corresponding International Application No. PCT/JP2017/012513, with an English translation.

* cited by examiner

PHOTOACOUSTIC MEASUREMENT APPARATUS

CROSS-REFERENCE TO RELATED APPLICATIONS

This application is a continuation application of International Application No. PCT/JP2017/012513, filed Mar. 28 2017, the disclosure of which is incorporated herein by reference in its entirety. Further, this application claims priority from Japanese Patent Application No. 2016-066025, filed Mar. 29, 2016, the disclosure of which is incorporated herein by reference in its entirety.

BACKGROUND OF THE INVENTION

1. Field of the Invention

The present invention relates to a photoacoustic measurement apparatus that measures photoacoustic waves generated in a subject, and more particularly, to a photoacoustic measurement apparatus that measures photoacoustic waves generated from a leading end of an insert inserted into a subject and enables a user to check the position of the leading end of the insert.

2. Description of the Related Art

Photoacoustic imaging for capturing an image of the inside of a living body using a photoacoustic effect has been known as a kind of image examination method capable of examining the state of the inside of the living body in a non-invasive manner. In a case in which the inside of the living body is irradiated with pulsed laser light such as a laser pulse, living tissues absorb the energy of the pulsed laser light and ultrasonic waves (photoacoustic waves) are generated by adiabatic expansion caused by the energy. In general, in photoacoustic imaging, the photoacoustic waves are detected by an ultrasound probe and a photoacoustic image is formed on the basis of a detection signal. In this way, it is possible to visualize the inside of the living body.

In the related art, various puncture needles are inserted into a subject that is a living body to perform a surgical operation, to collect a sample, and to perform a treatment such as the injection of a medical solution.

In a case in which various treatments are performed using the puncture needle, a configuration that enables a user to check the position of a leading end of the puncture needle is preferable for the safety of the subject. JP2015-37519A discloses a technique that applies the photoacoustic imaging to enable the user to check the position of a leading end of an insert such as a puncture needle. JP2015-37519A discloses a configuration in which a light guide member, such as an optical fiber, that reaches the vicinity of the leading end of the insert, is provided in the insert, such as the puncture needle, a light absorption member covering the leading end of the light guide member is provided at the leading end of the insert, and light propagated through the light guide member is incident on the light absorption member from the leading end of the light guide member. Light from the leading end of the light guide member is incident on the light absorption member and the light absorption member generates photoacoustic waves. The photoacoustic waves are detected and a photoacoustic image of the light absorption member is displayed. Therefore, it is possible to check the leading end of the light guide member, that is, the leading end of the insert.

SUMMARY OF THE INVENTION

In the configuration disclosed in JP2015-37519A, in a case in which the light guide member, such as an optical fiber, is damaged or in a case in which the light guide member and the light absorption member are disconnected from each other, light for generating photoacoustic waves leaks from the leading end of the insert to the outside. It is not preferable that an operator or a subject is unnecessarily exposed to the leakage light from the insert. In a case in which, for example, the disconnection between the light guide member and the light absorption member or the missing of a part of the light absorption member occurs, the position where photoacoustic waves are generated deviates or the signal intensity of photoacoustic waves is reduced. As a result, there is a concern that the position of the leading end of the insert in the subject will not be accurately detected. In a case in which a sufficient amount of excitation light does not reach the leading end of the light guide member due to, for example, the cutting of a part of the light guide member, it is difficult to generate sufficient photoacoustic waves. Therefore, it is difficult to detect the position where photoacoustic waves are generated. As a result, it is difficult to accurately detect the position of the leading end of the insert.

The invention has been made in view of the above-mentioned problems and an object of the invention is to provide a photoacoustic measurement apparatus that can detect a failure of a photoacoustic wave generation unit including a light guide member and a light absorption member.

According to the invention, there is provided a photoacoustic measurement apparatus comprising: a main light source that emits pulsed laser light; a sub-light source that emits light with a wavelength different from a wavelength of the pulsed laser light; a light guide member that is connected to the main light source and the sub-light source so as to be switchable between the main light source and the sub-light source and guides the light which has been emitted from the main light source and the sub-light source and has been incident on a base end to a leading end; an insert of which at least a leading end portion is inserted into a subject and which includes at least the leading end of the light guide member and a light absorption member that is connected to the leading end, absorbs the pulsed laser light, and generates photoacoustic waves; and a photoacoustic wave detection unit that detects the photoacoustic waves emitted from the leading end portion of the insert inserted into the subject. The photoacoustic measurement apparatus has, as an operation mode, a failure detection mode that drives the sub-light source and detects a failure of a photoacoustic wave generation unit including the light guide member and the light absorption member.

Preferably, the photoacoustic measurement apparatus according to the invention further comprises a protective member that includes a portion of the light guide member which is not included in the insert. Preferably, the protective member transmits the light emitted from the sub-light source.

Preferably, the photoacoustic measurement apparatus according to the invention further comprises: a light detection unit that detects leakage light from the leading end portion of the insert; and a determination unit that determines the failure of the photoacoustic wave generation unit on the basis of an amount of leakage light detected by the light detection unit.

Preferably, in the photoacoustic measurement apparatus according to the invention, the light detection unit comprises an optical filter that transmits only a wavelength range of the light emitted from the sub-light source and is provided on a light incident surface.

Preferably, in the photoacoustic measurement apparatus according to the invention, the determination unit determines that the failure has occurred in the photoacoustic wave generation unit in a case in which the amount of leakage light detected by the light detection unit is greater than a predetermined reference value.

Preferably, the photoacoustic measurement apparatus according to the invention further comprises: a failure notification unit that notifies the failure in a case in which the determination unit determines that the failure has occurred in the photoacoustic wave generation unit.

Preferably, in the photoacoustic measurement apparatus according to the invention, the failure detection mode ends in a case in which no failure is detected in the failure detection mode for a predetermined period of time.

Preferably, the photoacoustic measurement apparatus according to the invention further comprises a main light source driving notification unit that indicates that the main light source is driven.

Preferably, the photoacoustic measurement apparatus according to the invention further comprises: an optical coupling unit for a main light source which is connected to the light guide member and through which the light guide member is optically coupled to the main light source; and an optical coupling unit for a sub-light source which is connected to the light guide member and through which the light guide member is optically coupled to the sub-light source.

Preferably, the photoacoustic measurement apparatus according to the invention further comprises a main light source connection detection unit that detects a connection between the light guide member and the optical coupling unit for a main light source.

Preferably, in the photoacoustic measurement apparatus according to the invention, the main light source is capable of being driven only in a case in which the main light source connection detection unit detects the connection between the light guide member and the optical coupling unit for a main light source. That is, preferably, the main light source is not driven in a case in which the main light source connection detection unit does not detect the connection between the light guide member and the optical coupling unit for a main light source.

Preferably, the photoacoustic measurement apparatus according to the invention further comprises a connection notification unit that, in a case in which the main light source connection detection unit detects the connection between the light guide member and the optical coupling unit for a main light source, notifies an external apparatus of the connection.

Preferably, the photoacoustic measurement apparatus according to the invention further comprises a sub-light source connection detection unit that detects a connection between the light guide member and the optical coupling unit for a sub-light source.

Preferably, in the photoacoustic measurement apparatus according to the invention, the sub-light source is capable of being driven only in a case in which the sub-light source connection detection unit detects the connection between the light guide member and the optical coupling unit for a sub-light source. That is, preferably, the sub-light source is not driven in a case in which the sub-light source connection detection unit does not detect the connection between the light guide member and the optical coupling unit for a sub-light source.

Preferably, the photoacoustic measurement apparatus according to the invention further comprises: an optical path coupling member comprising a first light input unit that is optically connected to the main light source, a second light input unit that is optically connected to the sub-light source, and one light output unit; and an optical coupling unit that is connected to the light guide member, the light guide member being optically coupled to the main light source and the sub-light source through the optical coupling unit and the optical path coupling member.

Preferably, the photoacoustic measurement apparatus according to the invention further comprises a connection detection unit that detects a connection between the light guide member and the optical coupling unit in a case in which the optical path coupling member and the optical coupling unit are provided.

Preferably, the main light source or the sub-light source is capable of being driven only in a case in which the connection detection unit detects the connection between the light guide member and the optical coupling unit. That is, preferably, neither the main light source nor the sub-light source is driven in a case in which the connection detection unit does not detect the connection between the light guide member and the optical coupling unit.

Preferably, the photoacoustic measurement apparatus according to the invention further comprises a mode switch that switches the failure detection mode between on and off.

Preferably, in the photoacoustic measurement apparatus according to the invention, the failure detection mode starts, using the detection of the connection between the light guide member and the optical coupling unit for a sub-light source by the sub-light source connection detection unit as a mode switch.

Preferably, in the photoacoustic measurement apparatus according to the invention, the failure detection mode starts, using the detection of the connection between the light guide member and the optical coupling unit by the connection detection unit as a mode switch.

The photoacoustic measurement apparatus according to the invention includes the sub-light source that emits light with a wavelength different from the wavelength of the pulsed laser light emitted from the main light source and has the failure detection mode that drives the sub-light source as the operation mode. Therefore, it is possible to easily check a failure of the photoacoustic wave generation unit including the light guide member and the light absorption member.

DESCRIPTION OF THE PREFERRED EMBODIMENTS

Hereinafter, embodiments of the invention will be described in detail with reference to the drawings.

Figure 1:
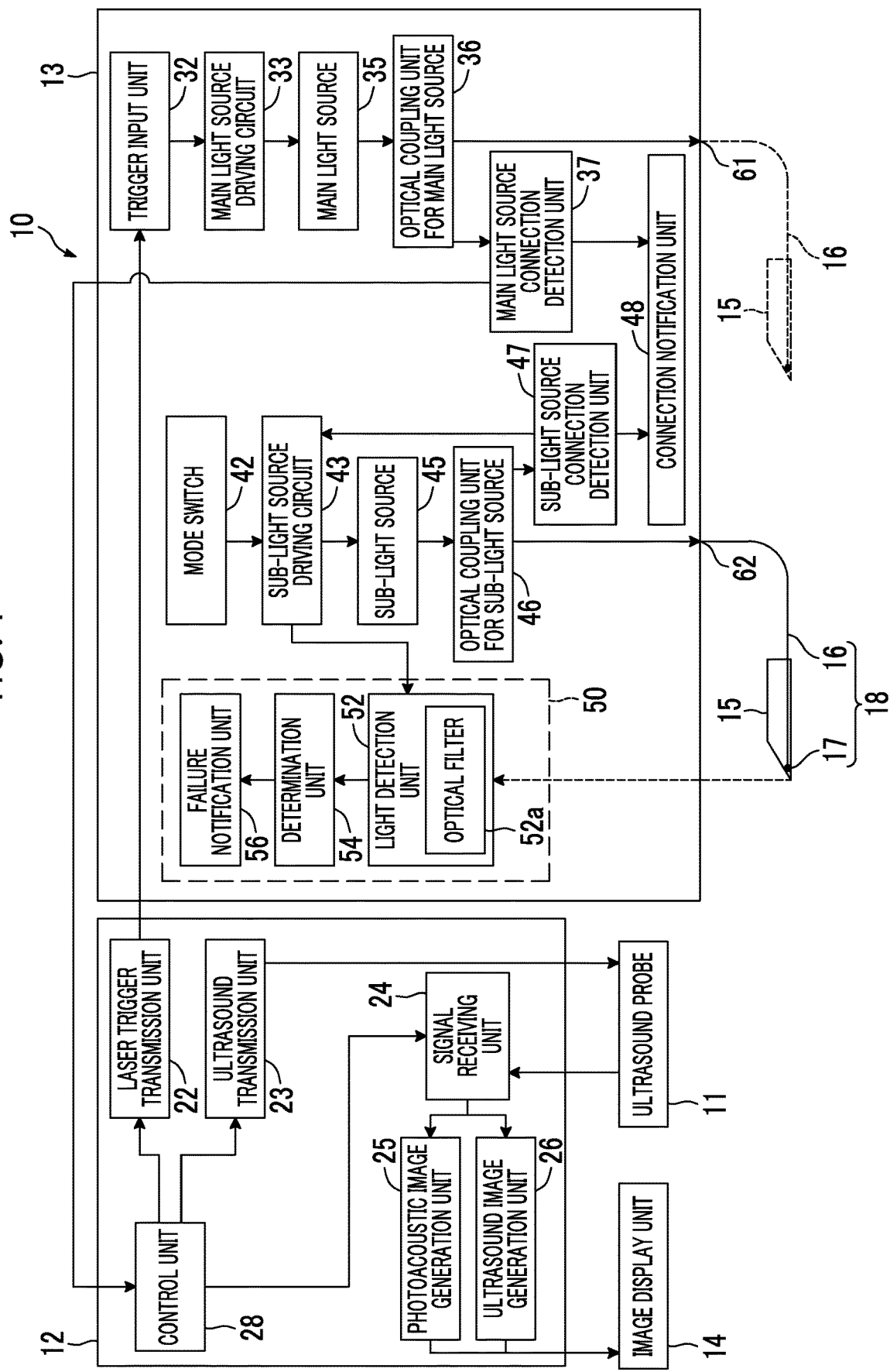
FIG. 1 is a block diagram illustrating a photoacoustic measurement apparatus according to a first embodiment of the invention.

FIG. 1 is a block diagram illustrating the configuration of a photoacoustic measurement apparatus 10 according to an embodiment.

For example, the photoacoustic measurement apparatus 10 has a function of generating a photoacoustic image on the basis of a photoacoustic signal and includes an ultrasound probe 11, an ultrasound unit 12, a laser unit 13, an image display unit 14, and a puncture needle 15 which is an example of an insert. A light absorption member 17 that generates photoacoustic waves is provided in the vicinity of a leading end of the puncture needle 15. A long light guide member 16, such as an optical fiber, that guides light to the light absorption member 17 has a base end connected to the laser unit 13.

The photoacoustic measurement apparatus 10 is configured such that it detects the photoacoustic waves emitted from the leading end of the puncture needle 15 inserted into a subject, using the probe 11, and converts the photoacoustic waves into a photoacoustic image to detect the position of the leading end of the puncture needle 15. The light absorption member 17 is irradiated with light guided by the light guide member 16. The light absorption member 17 absorbs the light and generates photoacoustic waves. In general, pulsed laser light is used to generate photoacoustic waves. For example, a failure occurs in a photoacoustic generation unit due to the damage of the light guide member 16, the disconnection between the light guide member 16 and the light absorption member 17, or the missing or breaking-off of a part of the light absorption member 17. In a case in which these failures occur and laser light is input to a photoacoustic wave generation unit 18, a portion of the laser light leaks to the outside and an operator and a subject are exposed to unnecessary laser light, which is not preferable.

The photoacoustic measurement apparatus 10 includes a failure detector for detecting a failure of the photoacoustic wave generation unit 18 including the light guide member 16 and the light absorption member 17, has, as an operation mode, a failure detection mode that detects the failure of the photoacoustic wave generation unit 18, and can prevent the use of the puncture needle 15 provided with the photoacoustic wave generation unit 18 in which a failure has occurred.

The laser unit 13 includes a main light source 35 that emits pulsed laser light and a sub-light source 45 that emits light with a wavelength different from the wavelength of the pulsed laser light emitted from the main light source 35. The main light source 35 is a light source for generating photoacoustic waves and is used in a photoacoustic measurement process for measuring photoacoustic waves. The sub-light source 45 is a light source that is used in the failure detection mode that inspects whether a failure occurs in the photoacoustic wave generation unit 18.

Hereinafter, each component of the apparatus 10 will be described.

Figure 2:
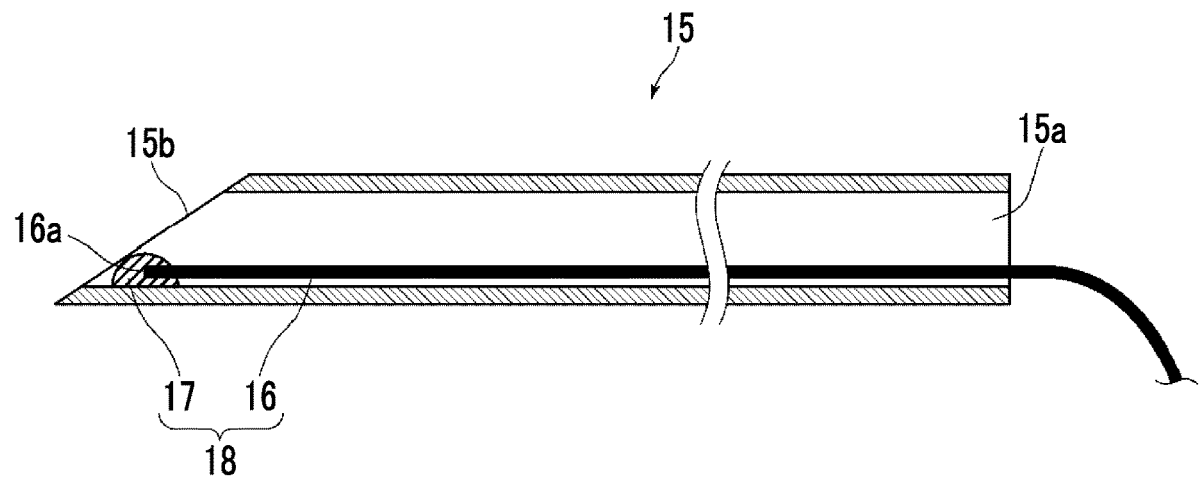
FIG. 2 is a cross-sectional view illustrating a puncture needle.

As described above, the puncture needle 15 is an example of the insert of which at least a leading end portion is inserted into the subject. FIG. 2 is a diagram illustrating the cross-section of the puncture needle 15. The puncture needle 15 is a needle tube having a hollow tube shape which is made of metal, such as stainless steel, or a synthetic resin. The puncture needle 15 has a hollow portion 15a that extends in the axial direction of the tube over the entire length. In addition, the puncture needle 15 has a leading end 15b that is cut obliquely with respect to the axis of the tube. The leading end 15b of the puncture needle 15 is inserted into the subject first.

The long light guide member 16 that guides the light for generating photoacoustic waves which has been input to the base end to a leading end 16a is provided in the hollow portion 15a such that the leading end 16a is located in the vicinity of the leading end 15b of the puncture needle. In the specification, one end of the long light guide member 16 to which light is input is referred to as a base end and the other end from which light is emitted is referred to as a leading end. The light absorption member 17 that is connected to the leading end 16a of the light guide member 16 is disposed in the vicinity of the leading end 15b of the puncture needle. Here, the vicinity of the leading end 15b of the puncture needle means a position where the light absorption member 17 can generate photoacoustic waves capable of imaging the leading end of the puncture needle 15 with accuracy required for a needling operation in a case in which the light absorption member 17 is disposed at the position. For example, the vicinity of the leading end is the range of 0 mm to 0.5 mm from the leading end to the base end of the puncture needle 15.

The light absorption member 17 is made of a material that absorbs light emitted from the main light source. A light absorption member may be used which is formed by inserting a pigment that absorbs light in a specific wavelength range, such as an ultraviolet range, a visible range, or an infrared range, into a resin according to the wavelength of light emitted from the main light source. For example, in a case in which the light emitted from the main light source is infrared light, a light absorption member can be used which is made of a synthetic resin, such as an epoxy resin, a fluorine resin, or a polyurethane resin with which a black pigment is mixed, is supplied to the inner wall of the puncture needle 15 in a molten state so as to cover the leading end 16a of the light guide member 16, and is solidified. In addition, as the pigment that absorbs light in a specific wavelength range, for example, pigments that are produced by FEW CHEMICALS GmbH or QCR Solutions Corp. and are commercially available can be appropriately used. In this example, a portion of the light guide member 16 in the vicinity of the leading end is fixed to the inner wall of the puncture needle 15 by the light absorption member 17. The other portion of the light guide member 16 may be appropriately fixed to the inner wall of the puncture needle by, for example, other adhesives.

The light guide member 16 is, for example, an optical fiber. The light guide member 16 may be one optical fiber that is continuous from a base end to a leading end or may be formed by connecting a plurality of optical fibers in series using, for example, optical connectors.

In a case in which the base end of the light guide member 16 is optically connected to the main light source 35 of the laser unit 13, laser light emitted from the main light source 35 is input to the base end of the light guide member 16. The laser light is emitted from the leading end 16a of the light guide member 16 and the light absorption member 17 is irradiated with the laser light. The light absorption member 17 absorbs the emitted pulsed laser light and generates photoacoustic waves.

A portion of the light guide member 16 which is not included in the puncture needle 15 is included in a flexible protective member 19 (see FIG. 3) such as a protective tube. It is preferable that the protective member 19 is transparent with respect to light emitted from the sub-light source. In this case, it is easy to visually check whether the light guide member 16 is damaged.

The ultrasound probe 11 is a photoacoustic wave detection unit that detects the photoacoustic waves emitted from the leading end portion of the insert (here, the puncture needle 15) inserted into the subject. The probe 11 has, for example, a plurality of ultrasound transducers that are one-dimensionally arranged. The probe 11 performs the transmission of acoustic waves (ultrasonic waves) to the subject and the reception of the reflected acoustic waves (reflected ultrasonic waves) with respect to the transmitted ultrasonic waves, in addition to the detection of the photoacoustic waves. With this configuration, it is possible to acquire ultrasound image data as well as photoacoustic image data.

The ultrasound unit 12 includes a laser trigger transmission unit 22, an ultrasound transmission unit 23, a signal receiving unit 24, a photoacoustic image generation unit 25, an ultrasound image generation unit 26, and a control unit 28 that controls there units.

The laser trigger transmission unit 22 receives a command from the control unit 28 and transmits a laser trigger to the laser unit 13.

The ultrasound transmission unit 23 receives an ultrasound transmission trigger signal from the control unit 28 and directs the probe 11 to transmit ultrasonic waves.

The signal receiving unit 24 receives a detection signal of the photoacoustic waves and a detection signal of the reflected ultrasonic waves detected by the probe 11. The signal receiving unit 24 starts to sample the photoacoustic waves or the reflected ultrasonic waves on the basis of a sampling trigger signal and a sampling clock signal from the control unit 28 and samples the detection signal of the photoacoustic waves or the reflected ultrasonic waves with a predetermined sampling period.

The photoacoustic image generation unit 25 generates a photoacoustic image on the basis of the detection signal of the photoacoustic waves detected by the probe 11. The generation of the photoacoustic image includes, for example, image reconfiguration, such as phasing addition, detection, and logarithmic conversion. The photoacoustic image generation unit 25 outputs data of the generated photoacoustic image to the image display unit 14.

The ultrasound image generation unit 26 generates an ultrasound image (reflected acoustic image) on the basis of the detection signal of the reflected ultrasonic waves detected by the probe 11. The generation of the ultrasound image includes, for example, image reconfiguration, such as phasing addition, detection, and logarithmic conversion. The ultrasound image generation unit 26 outputs data of the generated ultrasound image to the image display unit 14.

The control unit 28 controls each component in the ultrasound unit 12. For example, in a case in which a photoacoustic image is acquired, the control unit 28 transmits a laser trigger signal to the laser unit 13 through the laser trigger transmission unit 22 such that the main light source 35 emits pulsed laser light. Then, the control unit 28 transmits a sampling trigger signal to the signal receiving unit 24 to start the sampling of photoacoustic waves with the emission of the pulsed laser light.

In a case in which an ultrasound image is acquired, the control unit 28 transmits an ultrasound transmission trigger signal for commanding the transmission of ultrasonic waves to the ultrasound transmission unit 23 such that the ultrasound transmission unit 23 directs the probe 11 to transmit ultrasonic waves. Then, the control unit 28 transmits a sampling trigger signal to the signal receiving unit 24 in synchronization with the transmission of the ultrasonic waves to start the sampling of the reflected ultrasonic waves.

The image display unit 14 individually displays the photoacoustic image and the ultrasound image or displays a composite image of the photoacoustic image and the ultrasound image on the basis of the data input from the ultrasound unit 12.

The laser unit 13 includes a trigger input unit 32, a main light source driving circuit 33, an optical coupling unit 36 for a main light source, and a main light source connection detection unit 37 as main light source driving means including the main light source 35. In addition, the laser unit 13 includes a mode switch 42 that switches a failure detection mode, which will be described below, between on and off. Further, the laser unit 13 includes a sub-light source driving circuit 43, an optical coupling unit 46 for a sub-light source, and a sub-light source connection detection unit 47 as sub-light source driving means including the sub-light source 45. Furthermore, the laser unit 13 includes a light detection unit 52 that detects light output from the sub-light source 45, a determination unit 54, and a failure notification unit 56 as failure detection means 50. The light detection unit 52 has an optical filter 52a that transmits the wavelength range of light output from the sub-light source 45 on a light incident surface. The failure detector for detecting the failure of the photoacoustic wave generation unit 18 includes sub-light source driving means and the failure detection means 50.

First, the main light source driving means including the main light source 35 will be described.

The main light source 35 is a flash lamp pumped Q-switch solid-state laser, such as an alexandrite laser or a yttrium aluminum garnet (YAG) laser, and emits, for example, laser light with a wavelength in a near-infrared wavelength range (greater than 700 nm) as measurement light emitted to the subject. The main light source 35 receives a trigger signal from the control unit 28 of the ultrasound unit 12 and outputs pulsed laser light.

Similarly, the main light source 35 may be configured using a yttrium aluminum garnet-second harmonic generation (YAG-SHG)-optical parametric oscillation (OPO) laser or a titanium sapphire (Ti-sapphire) laser that can output laser light in the near-infrared wavelength range in addition to the alexandrite laser.

The wavelength band of the pulsed laser light emitted from the main light source 35 is not limited to the near-infrared range and may be a visible or ultraviolet wavelength band.

The main light source 35 is not limited to the solid-state laser light source and may be other types of laser light sources. For example, the main light source 35 may be a laser diode light source (semiconductor laser light source) or an optical-amplification-type laser light source having a laser diode light source as a seed light source.

For example, in a case in which the main light source 35 is an optical-amplification-type laser light source, the main light source 35 may include a semiconductor laser light source that emits pulsed laser light as seed light, an excitation semiconductor laser light source that emits excitation laser light, a multiplexer that multiplexes the pulsed laser light and the excitation laser light, an optical fiber amplifier that has a core doped with, for example, erbium (Er) and is connected to the multiplexer, an optical isolator that is connected to the optical fiber amplifier and is used to prevent oscillation, and an optical wavelength conversion element that converts the pulsed laser light output from the optical isolator into a second harmonic with a wavelength that is half the wavelength of the pulsed laser light.

The trigger input unit 32 receives a laser trigger signal from the ultrasound unit 12 and transmits the laser trigger signal to the main light source driving circuit 33. The main light source driving circuit 33 receives the laser trigger signal and drives the main light source 35 such that laser light is emitted from the main light source 35 at a desired time. The optical coupling unit 36 for a main light source includes a focusing optical system and an optical connector for making light from the main light source 35 incident on the light guide member 16. The main light source connection detection unit 37 detects the connection of the light guide member 16 to the optical coupling unit 36 for a main light source. In the photoacoustic measurement apparatus 10, the measurement of the photoacoustic waves from the leading end portion of the puncture needle is performed in a state in which (a state represented by a dashed line in FIG. 1) the light guide member 16 is connected to the optical coupling unit 36 for a main light source and is optically coupled to the main light source. For example, the main light source connection detection unit 37 detects the connection using a contact of a microswitch that is provided in a connection portion 61 between the light guide member 16 and the optical coupling unit 36 for a main light source.

Preferably, only in a case in which the light guide member 16 is connected to the optical coupling unit 36 for a main light source, the main light source 35 can be driven. That is, in a case in which the light guide member 16 is not connected to the optical coupling unit 36 for a main light source, the main light source 35 is not driven. In the apparatus 10, in a case in which the main light source connection detection unit 37 detects the connection between the light guide member 16 and the optical coupling unit 36 for a main light source, the main light source connection detection unit 37 transmits a connection detection signal to the ultrasound unit 12. In a case in which the ultrasound unit 12 does not receive the connection detection signal, the control unit 28 does not transmit the laser trigger signal. In a case in which the light guide member 16 is not connected to the optical coupling unit 36 for a main light source, the control unit 28 stops the transmission of the laser trigger signal. The main light source 35 is not driven in a state in which the light guide member 16 is not connected to the optical coupling unit 36 for a main light source. Therefore, even in a case in which the main light source 35 is a laser light source, the user can stably inspect the photoacoustic wave generation unit 18, which is preferable.

The mode switch 42 is a switch that switches the failure detection mode between on and off. In a state in which the failure detection mode is turned on, the light detection unit 52 is driven and waits for a light detection start command for a predetermined period for failure detection or detects light. In a state in which the failure detection mode is turned off, the light detection unit 52 is not driven. In a case in which the mode switch 42 is provided, the user can control the turn-on and turn-off the failure detection mode. Therefore, the user can stably inspect the photoacoustic wave generation unit 18. In addition, the mode switch 42 may be provided in any one of the laser unit 13, the ultrasound unit 12, and the ultrasound probe 11 or may be provided as a separate unit. The mode switch 42 may have any configuration as long as it can receive the user's operation and can command the light detection unit 52 to start and end detection according to the received operation.

The photoacoustic measurement apparatus 10 is configured that, in a case in which the mode switch 42 is turned on, a driving start trigger signal is transmitted to the sub-light source driving circuit 43 and the sub-light source driving circuit 43 and the light detection unit 52 are operated. Here, the mode switch 42 also functions as a mode notification unit and includes a light emitting element that is covered with a transparent member. The mode switch 42 is turned on in a case in which the failure detection mode is turned on and is turned off in a case in which the failure detection mode is turned off. In a case in which the mode notification unit is provided, the user can easily recognize the operation mode, which is preferable. In addition, the mode notification unit may be omitted or may be provided separately from the mode switch 42. The mode switch 42 may be provided in any one of the laser unit 13, the ultrasound unit 12, and the ultrasound probe 11 or may be provided as a separate unit.

The mode switch is a manual switch that is manually turned on and off by the user. However, an automatic switch that automatically switches the mode on the basis of various criteria, such as the connection state of an apparatus and predetermined time conditions, may be provided.

As an aspect of the manual switch, for example, the failure detection mode may be designated through a menu screen displayed on the image display unit 14. A configuration in which the failure detection mode starts, using the detection of the connection of the light guide member 16 to the optical coupling unit 46 for a sub-light source as a trigger, is given as an example of the automatic switch. In addition, as the setting of automatic mode switching, the failure detection mode may automatically end in a case in which no failure has been detected in the failure detection mode. However, it is preferable that the failure detection mode does not automatically end without the input of user confirmation in a case in which a failure has been detected in the failure detection mode.

Next, the sub-light source driving means including the sub-light source 45 will be described.

The sub-light source 45 is a light emitting element, such as a light emitting diode or a laser diode, and is kept on or blinks. Light emitted from the sub-light source 45 may have a wavelength different from the wavelength of pulsed laser light emitted from the main light source. Light in a visible range (400 nm to 700 nm) is particularly preferable. The light in the visible range may be white light or light in a monochromatic wavelength band such as green (wavelength of 510 nm to 570 nm). In a case in which both light emitted from the main light source 35 and light emitted from the sub-light source 45 are in the visible range, it is assumed that the sub-light source 45 emits light with a wavelength different from the wavelength of light emitted from the main light source 35 in the visible range. The light components with different wavelengths in the visible range may be light components that can be visually distinguished from each other by colors. The light components may be, for example, red light and green light having wavelength ranges that do not overlap each other. Alternatively, light emitted from one light source may include a portion of or the entire wavelength range of light emitted from the other light source. For example, the light components may be white light and green light. The turn-on and turn-off the sub-light source 45 are controlled by the sub-light source driving circuit 43.

The sub-light source driving circuit 43 controls the turn-on and turn-off of the sub-light source 45 in response to a command input through the mode switch 42. The optical coupling unit 46 for a sub-light source includes a focusing optical system and an optical connector that make light from the sub-light source 45 incident on the light guide member 16. Therefore, the sub-light source connection detection unit 47 detects the connection of the light guide member 16 to the optical coupling unit 46 for a sub-light source. In the photoacoustic measurement apparatus 10, the failure detection mode that detects the failure of the photoacoustic wave generation unit 18 is performed in a state in which the light guide member 16 is connected to the optical coupling unit 46 for a sub-light source and is optically coupled to the sub-light source 45. Similarly to the main light source connection detection unit 37, the sub-light source connection detection unit 47 detects connection using a contact of, for example, a microswitch that is provided in a connection portion 62 between the light guide member 16 and the optical coupling unit 46 for a sub-light source.

Preferably, only in a case in which the light guide member 16 is connected to the optical coupling unit 46 for a sub-light source, the sub-light source 45 can be driven. That is, in a case in which the light guide member 16 is not connected to the optical coupling unit 46 for a sub-light source, the sub-light source 45 is not turned on. In the apparatus 10, in a case in which the sub-light source connection detection unit 47 detects the connection of the light guide member 16 to the optical coupling unit 46 for a sub-light source, the sub-light source connection detection unit 47 transmits a connection detection signal to the sub-light source driving circuit 43. The sub-light source driving circuit 43 is configured such that it does not drive the sub-light source 45 if a connection detection signal is not received from the sub-light source connection detection unit 47 even in a case in which the mode switch 42 is turned on.

The laser unit 13 further includes a connection notification unit 48 that notifies the user of the connection between the light guide member 16 and the optical coupling unit 36 for a main light source and the connection between the light guide member 16 and the optical coupling unit 46 for a sub-light source. The connection notification unit 48 may be, for example, a light emitting element such as a light emitting diode (LED). In a connected state, the light emitting element is turned on. In a non-connected state, the light emitting element is turned off. In this way, the user can visually check the connection state. A multi-color LED may be used as the connection notification unit 48. For example, red light may be emitted in a case in which the light guide member 16 is connected to the main light source. Green light may be emitted in a case in which the light guide member 16 is connected to the sub-light source. Yellow light may be emitted in a case in which the light guide member 16 is not connected to any light source.

In this embodiment, the connection notification unit 48 is provided in the laser unit 13. However, the connection notification unit 48 may be provided in any portion of the photoacoustic measurement apparatus 10. It is preferable that the connection notification unit 48 is provided in the vicinity of the connection portions 61 and 62 for connecting the light guide member 16 of the laser unit 13 for ease of check.

In this embodiment, the sub-light source driving circuit 43 operates in a case in which the mode switch 42 is turned on. However, the sub-light source driving circuit 43 may receive a trigger signal from the control unit 28 of the ultrasound unit 12 and then operate. Alternatively, in a case in which the sub-light source connection detection unit 47 detects the connection between the light guide member 16 and the optical coupling unit 46 for a sub-light source, the sub-light source driving circuit 43 may receive a connection detection signal from the sub-light source connection detection unit 47 and then operate. In addition, while the light guide member 16 is connected to the optical coupling unit 46 for a sub-light source, the sub-light source 45 may be driven. While the light guide member 16 is not connected to the optical coupling unit 46 for a sub-light source, the sub-light source 45 may not be driven.

Next, the failure detection means 50 will be described.

The light detection unit 52 is a photoelectric conversion element such as a photodiode that can detect light emitted from the main light source 35. The light detection unit 52 can be an element that can detect light emitted from the main light source 35 and may be a thermoelectric conversion element such as a thermopile. The light detection unit 52 operates an optical detection circuit in response to a sub-light source driving command from the sub-light source driving circuit 43 to start light detection and transmits the amount of detected light to the determination unit 54. The light detection unit 52 may start an accumulation operation for a predetermined period since the driving of the sub-light source 45 and may detect the amount of light. The predetermined period may be, for example, 10 sec to 30 sec. The light detection unit 52 may start detection in a case in which the main light source 35 starts to be driven or a case in which a proximity sensor that is separately provided detects an object in a predetermined distance range from the light detection unit 52. The optical filter 52a is a bandpass filter that cuts wavelengths other than the wavelength of light emitted from the sub-light source 45 in order to remove the influence of light other than the light emitted from the sub-light source.

The determination unit 54 determines whether a failure has occurred in the photoacoustic wave generation unit 18 on the basis of the amount of detected light received from the light detection unit 52. The determination unit 54 has a determination threshold value as a predetermined reference value and compares the amount of detected light with the determination threshold value to determine whether a failure has occurred in the photoacoustic wave generation unit 18. For example, in a case in which the amount of detected light is greater than the determination threshold value, the determination unit 54 determines that a failure has occurred in the photoacoustic wave generation unit 18. Since whether a failure has occurred is determined on the basis of the determination threshold value, it is possible to easily determine whether a failure has occurred.

The failure notification unit 56 notifies the user of the determination result of the determination unit 54. The failure notification unit 56 may be a light emitting element, such as an LED, or beep sound generation means. In a case in which the determination result indicates that "a failure has occurred (failure)", the light emitting element is kept on or blinks, or the beep sound generation means generates a beep sound. In a case in which the determination result indicates that "no failure has occurred (normal)", the notification may not be performed. In addition, for example, a method for turning on the light emitting element may be changed to notify the determination result or the beep sound generation means may generate a beep sound different from the beep sound indicating the failure to notify the determination result. Furthermore, a multi-color LED may be used as the light emitting element, red light may be emitted in a case in which a failure occurs, and green light may be emitted in a case in which no failure occurs. In addition, characters "failure detected" or a mark may be displayed on the image display unit 14. Furthermore, the light emitting element may blink for a failure determination period such that the user can check whether a failure is being determined.

The connection notification unit 48 may also function as the failure notification unit 56. In this configuration, in a case in which the determination unit 54 determines that a failure has occurred in the photoacoustic wave generation unit 18, the connection notification unit 48 may perform failure notification so as to be distinguished from the notification of the connection between the light guide member 16 and the optical coupling unit 36 for a main light source or the optical coupling unit 46 for a sub-light source. This configuration makes it possible to notify the user of the connection state and the detection result of a failure, without increasing the number of components. In addition, a multi-color LED may be used as the connection notification unit 48 and the connection notification unit 48 may emit different color light components depending on the situation. For example, the connection notification unit 48 may emit yellow light at the time of non-connection, may emit green light at the time of connection, and may emit red light at the time of failure notification.

Figure 3:
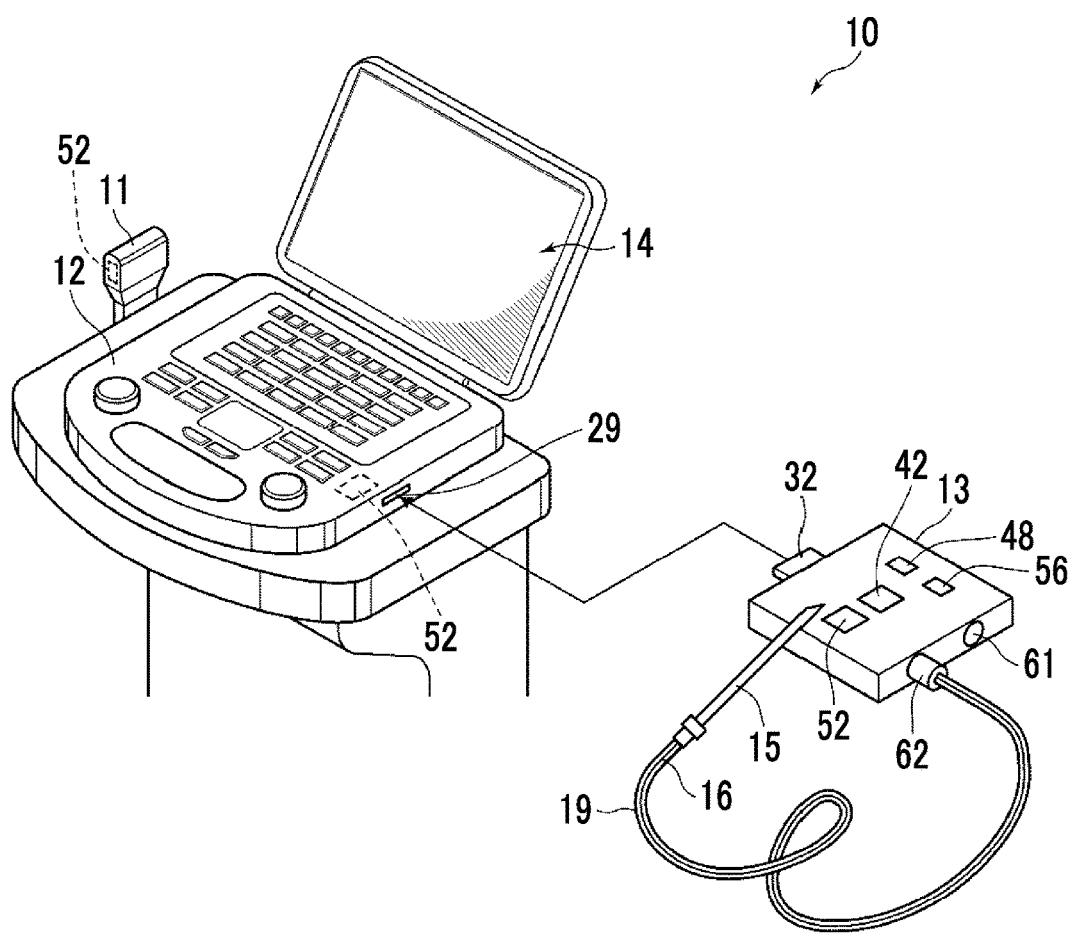
FIG. 3 is a diagram illustrating the outward appearance of the photoacoustic measurement apparatus including a laser unit.

FIG. 3 is a diagram illustrating the specific outward appearance of the photoacoustic measurement apparatus 10 according to the first embodiment of the invention.

As illustrated in FIG. 3, in the photoacoustic measurement apparatus 10, the ultrasound unit 12 is a computer including a processor, a memory, and an input unit and is integrated with the image display unit 14. A program that is related to the generation of a photoacoustic image and the generation of an ultrasound image and includes the laser trigger transmission unit 22, the ultrasound transmission unit 23, the signal receiving unit 24, the photoacoustic image generation unit 25, the ultrasound image generation unit 26, and the control unit 28 is incorporated into the ultrasound unit 12. The probe 11 is connected to the ultrasound unit 12 and the laser unit 13 is connected to the ultrasound unit 12 through a universal serial bus (USB) port which will be described below.

The laser unit 13 includes the connection portion 61 for a normal mode which is a connection port for connecting the light guide member 16 in the normal mode other than failure detection and the connection portion 62 for a failure detection mode which is a connection port for connecting the light guide member 16 in the failure detection mode. The light guide member 16 is attached to the connection portion 61 for a normal mode to be connected to the optical coupling unit 36 for a main light source. The light guide member 16 is attached to the connection portion 62 for a failure detection mode to be connected to the optical coupling unit 46 for a sub-light source.

The mode switch 42 and the light detection unit 52 are provided on the surface of the laser unit 13. In addition, the failure notification unit 56 and the connection notification unit 48 which are light emitting elements are provided on the surface of the laser unit 13.

The trigger input unit 32 of the laser unit 13 is connected to a signal output line of the ultrasound unit 12. A trigger input terminal of the trigger input unit 32 is, for example, a USB connector. The ultrasound unit 12 has a USB port (receptacle) 29. The USB connector including the trigger input terminal is inserted into the USB port 29 such that a signal output from the ultrasound unit 12 is supplied.

The process of the photoacoustic measurement apparatus 10 according to this embodiment having the above-mentioned configuration will be described.

Figure 4:
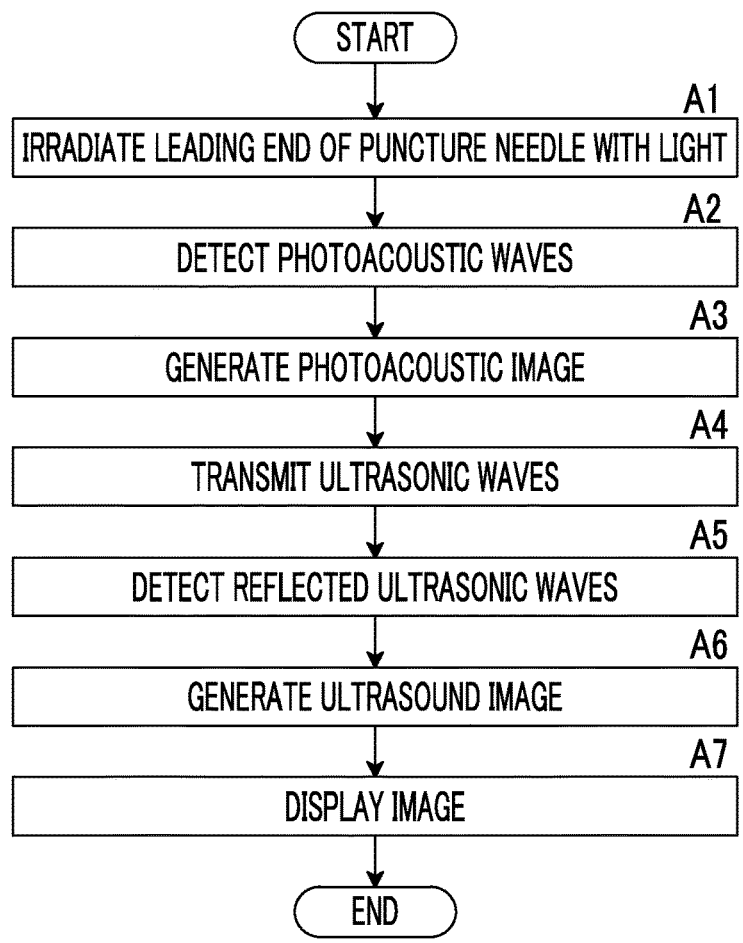
FIG. 4 is a flowchart illustrating a photoacoustic measurement process of the photoacoustic measurement apparatus according to the first embodiment.

FIG. 4 is a flowchart illustrating a photoacoustic measurement process of the photoacoustic measurement apparatus 10 according to the first embodiment. First, a photoacoustic wave measurement process of the photoacoustic measurement apparatus 10 will be described with reference to FIG. 4.

In the photoacoustic wave measurement process, image acquisition conditions, such as a frame rate, the number of laser beams per frame, and the balance of the number of frames of a reflected acoustic wave signal and a photoacoustic image signal per frame, are stored in a memory (not illustrated) of the ultrasound unit 12 in advance. Light source driving conditions, such as a laser light emission time, the number of laser pulses, and a current, are determined by the control unit 28 so as to correspond to the image acquisition conditions and are used by the main light source driving circuit 33 to drive the main light source 35.

The photoacoustic wave measurement process starts in a state in which the light guide member 16 is connected to the optical coupling unit 36 for a main light source. The control unit 28 of the ultrasound unit 12 transmits a trigger signal to the laser unit 13. In a case in which the trigger signal is received, the laser unit 13 starts laser oscillation and emits pulsed laser light. The pulsed laser light emitted from the laser unit 13 is guided to the vicinity of the leading end of the puncture needle 15 by the light guide member 16 and the light absorption member 17 is irradiated with the pulsed laser light. The light absorption member 17 absorbs the pulsed laser light and generates photoacoustic waves. In a photoacoustic measurement process, a user, such as a doctor, inserts the puncture needle 15 into the subject at any time, such as before and after the main light source 35 is driven.

The probe 11 detects the photoacoustic waves generated from the light absorption member 17 irradiated with the pulsed laser light (Step A2). The signal receiving unit 24 receives a photoacoustic wave detection signal from the probe 11, samples the photoacoustic wave detection signal, stores the sampled photoacoustic wave detection signal, and transmits the stored photoacoustic wave detection signal to the photoacoustic image generation unit 25 (Step A3). The photoacoustic image generation unit 25 generates a photoacoustic image on the basis of the photoacoustic wave detection signal and the photoacoustic image is displayed on the image display unit 14.

In the photoacoustic wave measurement process, an ultrasound image may be acquired after the photoacoustic image is acquired. An ultrasound image acquisition operation is performed as follows. The control unit 28 transmits an ultrasound transmission trigger signal to the ultrasound transmission unit 23 and the ultrasound transmission unit 23 directs the probe 11 to transmit ultrasonic waves in response to the ultrasound transmission trigger signal (Step A4). After transmitting the ultrasonic waves, the probe 11 detects reflected ultrasonic waves (Step A5). The signal receiving unit 24 receives a detection signal of the reflected ultrasonic waves, samples the reflected ultrasonic wave detection signal, stores the sampled reflected ultrasonic wave detection signal, and transmits the stored reflected ultrasonic wave detection signal to the ultrasound image generation unit 26. The ultrasound image generation unit 26 generates an ultrasound image on the basis of the reflected ultrasonic wave detection signal (Step A6) and the ultrasound image is displayed on the image display unit 14 (Step A7).

In addition, the image display unit 14 may combine the photoacoustic image and the ultrasound image and display a composite image. With this configuration, it is possible to check the position of the leading end 15b of the puncture needle 15 in a living body and thus to safely insert the puncture needle 15 with high accuracy. In addition, in the photoacoustic measurement apparatus 10, the acquisition of the ultrasound image data may be performed in another mode independently of the acquisition of the photoacoustic image data.

Figure 5:
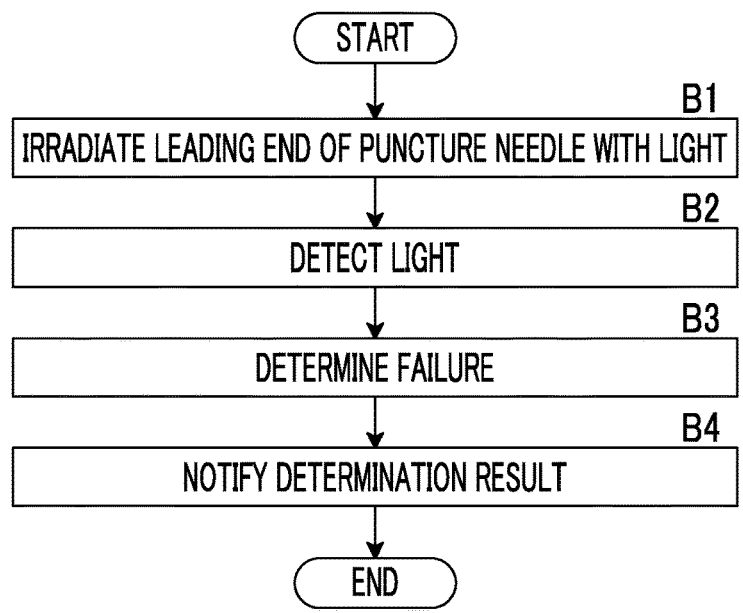
FIG. 5 is a flowchart illustrating a failure detection process of the photoacoustic measurement apparatus according to the first embodiment.

FIG. 5 is a flowchart illustrating a failure detection process of the photoacoustic measurement apparatus according to the first embodiment. The failure detection process of the photoacoustic measurement apparatus 10 in the failure detection mode will be described with reference to FIG. 5.

The user turns on the mode switch 42 to start the failure detection mode. The failure detection process starts in a state in which the light guide member 16 is connected to the optical coupling unit 46 for a sub-light source and the puncture needle 15 is not inserted into the subject. The sub-light source driving circuit 43 drives the sub-light source 45 and predetermined light is emitted from the sub-light source 45. The light emitted from the sub-light source 45 is guided to the vicinity of the leading end 15b of the puncture needle 15 by the light guide member 16 and the light absorption member is irradiated with the light (Step B1). In a case in which a failure, such as the detachment of the leading end 15b of the puncture needle 15 from the light absorption member 17, occurs, light leaks from the leading end 15b of the puncture needle 15.

Here, the light detection unit 52 is configured so as to detect light only in a case in which the conditions in which the optical coupling unit 46 for a sub-light source and the light guide member 16 are connected to each other and the failure detection mode is turned on are satisfied, on the basis of the connection notification signal of the sub-light source connection detection unit 47. Therefore, the failure detection process is performed in a state in which the user operates the mode switch 42 to turn on the failure detection mode and is not performed in a state in which the failure detection mode is turned off. In addition, the failure detection process is performed in a state in which the light guide member 16 is connected to the optical coupling unit 46 for a sub-light source and is not performed in a state in which the light guide member 16 is not connected to the optical coupling unit 46 for a sub-light source.

The light detection unit 52 detects light for a predetermined period since the start of the driving of the sub-light source on the basis of the trigger signal indicating the driving of the sub-light source 45 from the sub-light source driving circuit 43 (Step B2). The user holds the leading end 15b of the puncture needle 15 over the light detection unit 52 for at least a portion of the predetermined period. The failure notification unit 56 blinks green for a period from the start of light detection by the light detection unit 52 to the output of the determination result during determination.

In this embodiment, the light detection unit 52 starts to detect light on the basis of the trigger signal indicating the driving of the sub-light source 45 from the sub-light source driving circuit 43 and detects leakage light from the leading end 15b of the puncture needle 15 for a predetermined period. This configuration makes it possible for the user to smoothly perform the failure detection process with the driving of the sub-light source 45.

Any conditions can be set as the start condition in which the light detection unit 52 starts light detection for a predetermined period for failure detection. For example, the light detection unit 52 may start to detect light for a predetermined period since the detection of the connection between the light guide member 16 and the optical coupling unit 46 for a sub-light source by the sub-light source connection detection unit 47 on the basis of the detection of the connection and the determination unit 54 may determine whether a failure has occurred in the photoacoustic wave generation unit 18 on the basis of the amount of leakage light detected by the light detection unit 52 for the predetermined period.

As another example, for example, a failure detection start button may be provided in the ultrasound unit 12. In a case in which a detection signal indicating that the user has performed the operation of turning on the failure detection start button is transmitted, the light detection unit 52 may start to detect light. Alternatively, a proximity detection sensor (not illustrated) may be provided. In a case in which the proximity detection sensor transmits a detection signal indicating that the puncture needle 15 is in a predetermined distance range, the light detection unit 52 may start to detect light.

The sub-light source 45 is turned off by the sub-light source driving circuit 43 after the period for which the light detection unit 52 detects light expires. The sub-light source 45 may be turned off by the end of the failure detection mode or may be turned off by the end of the failure detection process.

Then, the accumulated amount of detected light is transmitted from the light detection unit 52 to the determination unit 54. The determination unit 54 compares the amount of detected light with a determination threshold value. The determination unit 54 determines that a failure has occurred in a case in which the input amount of detected light is greater than the determination threshold value and determines that no failure has occurred in a case in which the input amount of detected light is equal to or less than the determination threshold value (Step B3). Then, the failure notification unit 56 notifies the user of the determination result of the determination unit 54 (Step B4). The failure notification unit 56 emits red light in a case in which the determination result indicates that a failure has occurred and emits green light in a case in which the determination result indicates that no failure has occurred to notify the determination result. The failure detection process of the failure detector ends. In a case in which the failure notification unit 56 notifies that a failure has occurred, the user performs an operation corresponding to the notification such as an operation of replacing the puncture needle 15.

The photoacoustic measurement apparatus 10 may be configured such that, in a case in which the determination unit 54 determines that no failure has occurred in the photoacoustic wave generation unit 18 on the basis of the amount of leakage light detected by the light detection unit 52 for a predetermined period, the detection of light by the light detection unit 52 is stopped and the failure detection mode ends.

In a case in which the determination unit 54 determines that a failure has occurred, the failure notification unit 56 may perform failure notification requiring the user to input confirmation and may continuously perform the failure notification until confirmation input is received. In this case, it is preferable that the failure detection mode is maintained until confirmation input is received from the user. For example, a portion of the control unit 28 may also function as the failure notification unit 56. In a case in which the control unit 28 determines that a failure has occurred, the control unit 28 may display, on a display screen, a message "Please press a confirmation button to continue to measure photoacoustic waves" and a confirmation button and may continuously display the message and the confirmation button until confirmation input is received from the user. In addition, the following configuration is considered: until confirmation input is received, the control unit 28 directs the laser trigger transmission unit 22 to transmit a laser stop command such that the main light source 35 is not driven. In a case in which it is determined that a failure has occurred, the user is prompted to input confirmation and it is possible to improve safety in the use of the photoacoustic measurement apparatus 10.

In addition, the photoacoustic wave measurement process may be performed regardless of whether the failure detection mode is turned on or off. It is possible to check a failure of an insert and to perform the photoacoustic wave measurement process at any time. For example, in a state in which the failure detection mode is turned on, each of the photoacoustic wave measurement process and the failure detection process can be performed to detect a failure of the leading end 15*b* of the puncture needle 15 immediately before the puncture needle 15 is inserted into the subject.

The photoacoustic measurement apparatus 10 may include a laser output notification unit (main light source driving notification unit) which notifies that the main light source 35 is being driven, that is, laser light is being output. The laser output notification unit may be a light emitting element such as an LED. The failure notification unit 56 may also function as the laser output notification unit. For example, green light blinks to notify the output of laser and red light blinks to notify a failure. In addition, the laser output notification unit may blink whenever a trigger pulse is received from the trigger input unit.

In a case in which the laser output notification unit is provided, the user can easily recognize whether laser is output and it is possible to safely inspect the photoacoustic wave generation unit.

Various notification units, such as the failure notification unit 56, the connection notification unit 48, and the laser output notification unit, may be independently configured or one notification unit may have two or three functions.

In a case in which one notification unit notifies a plurality of information items, a multi-color LED may be used to emit different color light components for each information item or the information items may be distinguished from each other by continuous lighting and light blinking.

In this embodiment, various notification units, such as the failure notification unit 56, the connection notification unit 48, and the laser output notification unit, provided in the apparatus are light emitting elements. In addition, the various notification units may be various notification display means that display notices on the image display unit 14.

The photoacoustic measurement apparatus 10 may further include a main light source driving external switch such as a switch for switching the laser trigger signal between on and off. The external switch may be connected to the ultrasound unit 12 to input on and off signals to the control unit 28. Since the external switch is provided, the user can control the driving of the main light source 35. Therefore, it is possible to safely inspect the photoacoustic wave generation unit.

In the above-described embodiment, the laser unit 13 includes the main light source driving means, the sub-light source driving means, and the failure detection means 50. However, these means may be separately provided.

Figure 6:
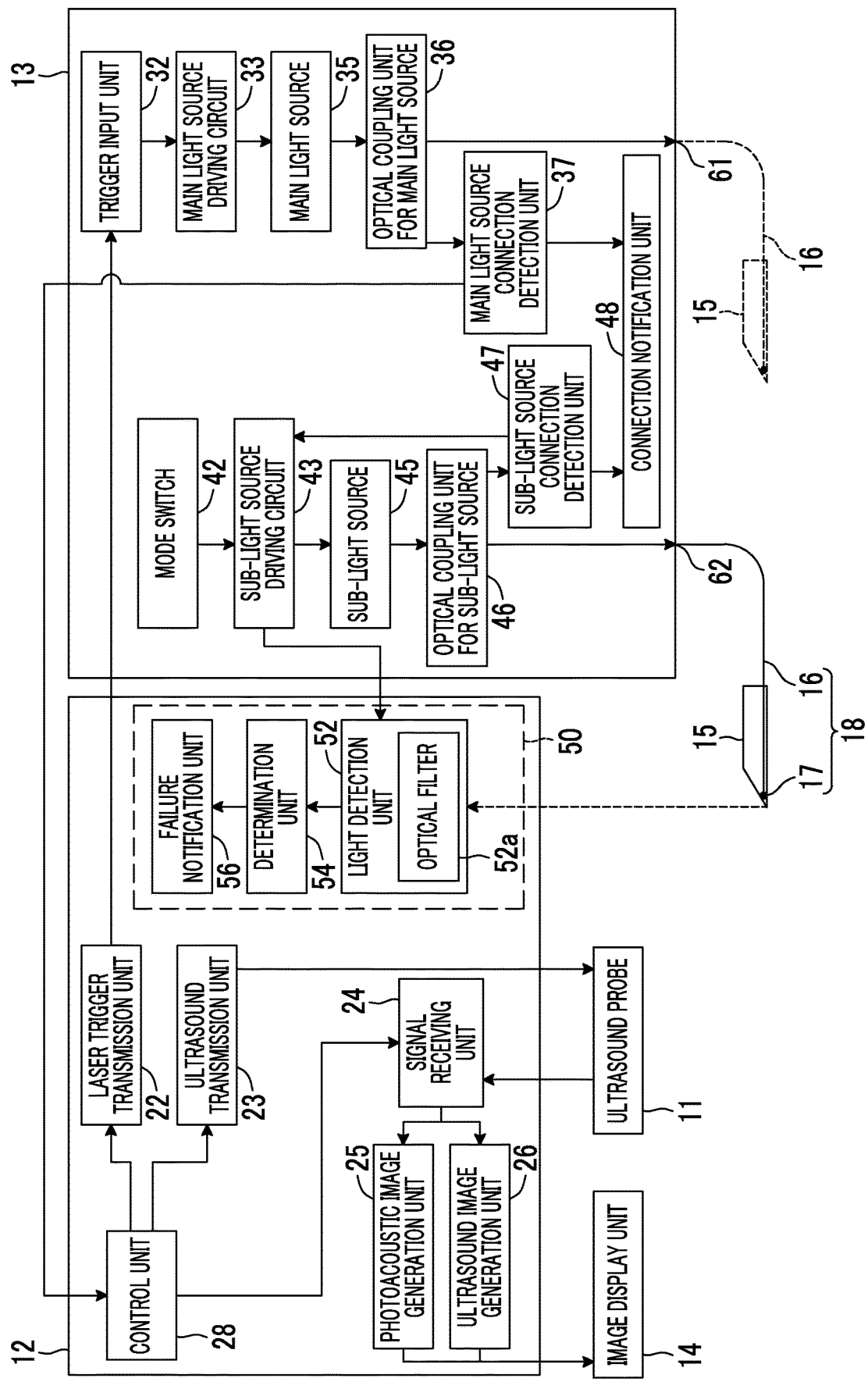
FIG. 6 is a block diagram illustrating design change example 1 of the photoacoustic measurement apparatus according to the first embodiment of the invention.
Figure 7:
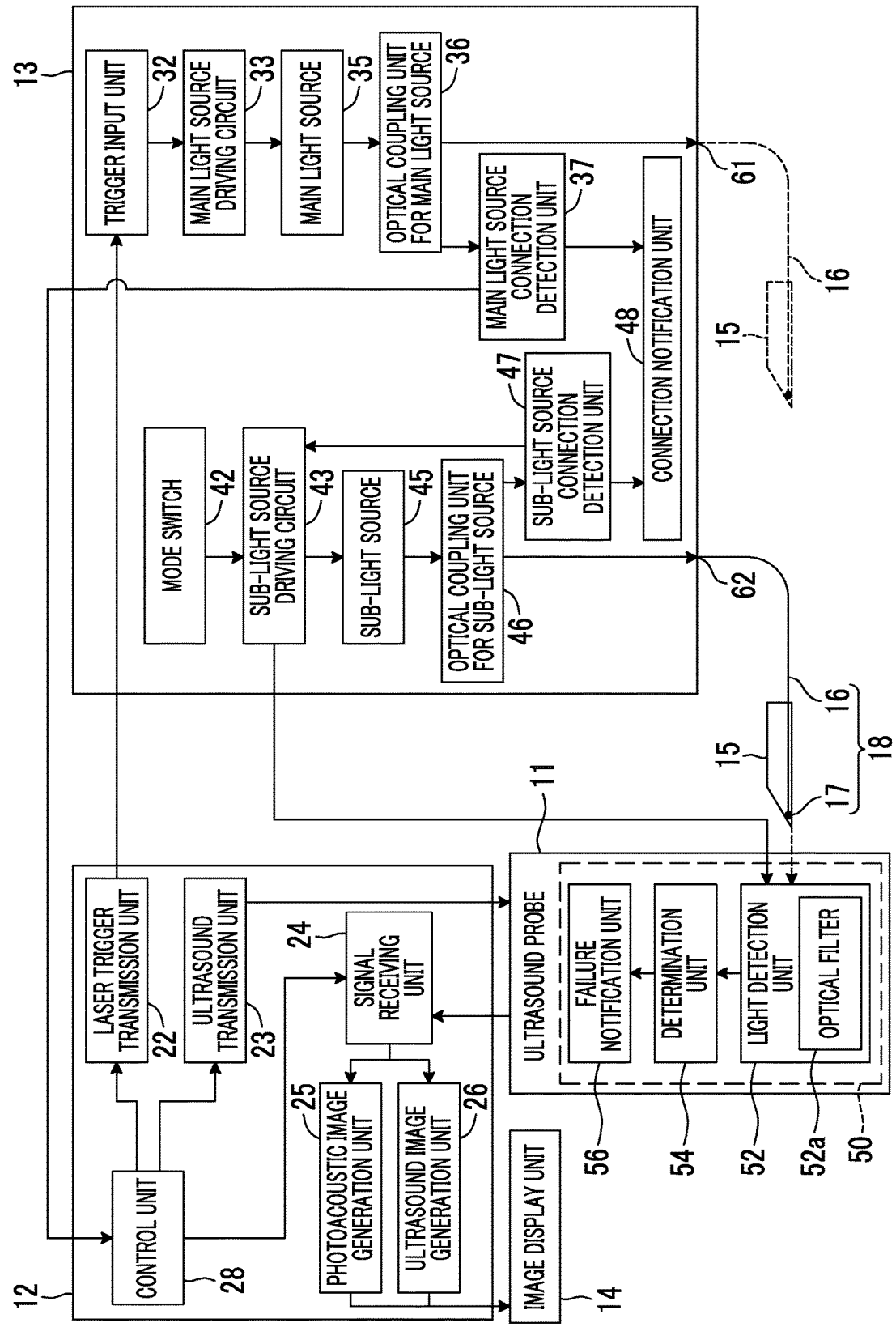
FIG. 7 is a block diagram illustrating design change example 2 of the photoacoustic measurement apparatus according to the first embodiment of the invention.

For example, FIGS. 6 and 7 illustrate design change example 1 and design change example 2 of the acoustic wave measurement apparatus 10 according to the first embodiment, respectively. As illustrated in FIG. 6 and, the laser unit 13 may include the main light source driving means and the sub-light source driving means and the ultrasound unit 12 or the probe 11 may include the failure detection means 50. In this case, for example, the light detection unit 52 is provided in a portion of the probe 11 or a portion of the ultrasound unit 12 as represented by a dashed line in FIG. 3. In addition, the light detection unit 52, the determination unit 54, and the failure notification unit 56 may be provided at different positions. For example, the light detection unit 52 is provided in the laser unit 13, the determination unit 54 is provided in the ultrasound unit 12, and the failure notification unit 56 is provided in the image display unit 14.

The configuration in which the failure detection means 50 including the light detection unit 52, the determination unit 54, and the failure notification unit 56 is provided in the ultrasound unit 12 as illustrated in FIG. 6 makes it easy for an assistant to the operator to perform an operation in a case in which a failure is detected.

Figure 8:
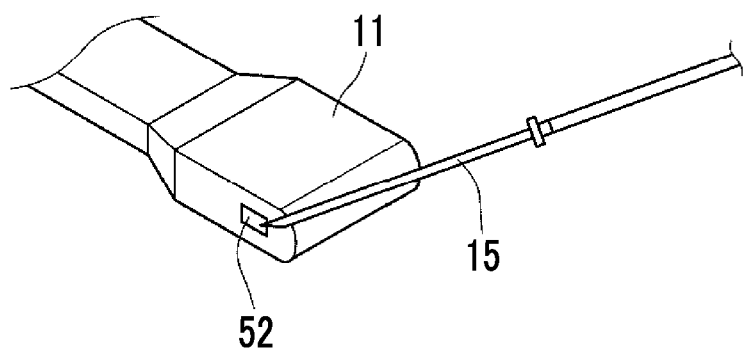
FIG. 8 is a diagram schematically illustrating the arrangement of a light detection unit in design change example 2 illustrated in FIG. 6.

FIG. 8 is a diagram schematically illustrating an example of the configuration in which the light detection unit 52 is provided in a portion of the ultrasound probe 11. In a case in which the light detection unit 52 is provided in a portion of the ultrasound probe 11 as illustrated in FIG. 8, the operator can manually detect a failure of the puncture needle 15. Both the ultrasound probe 11 and the puncture needle 15 need to be used in a clean environment. In a case in which the light detection unit 52 is provided in a portion of the ultrasound probe 11, a failure can be detected in a clean environment, which is particularly preferable.

Figure 9:
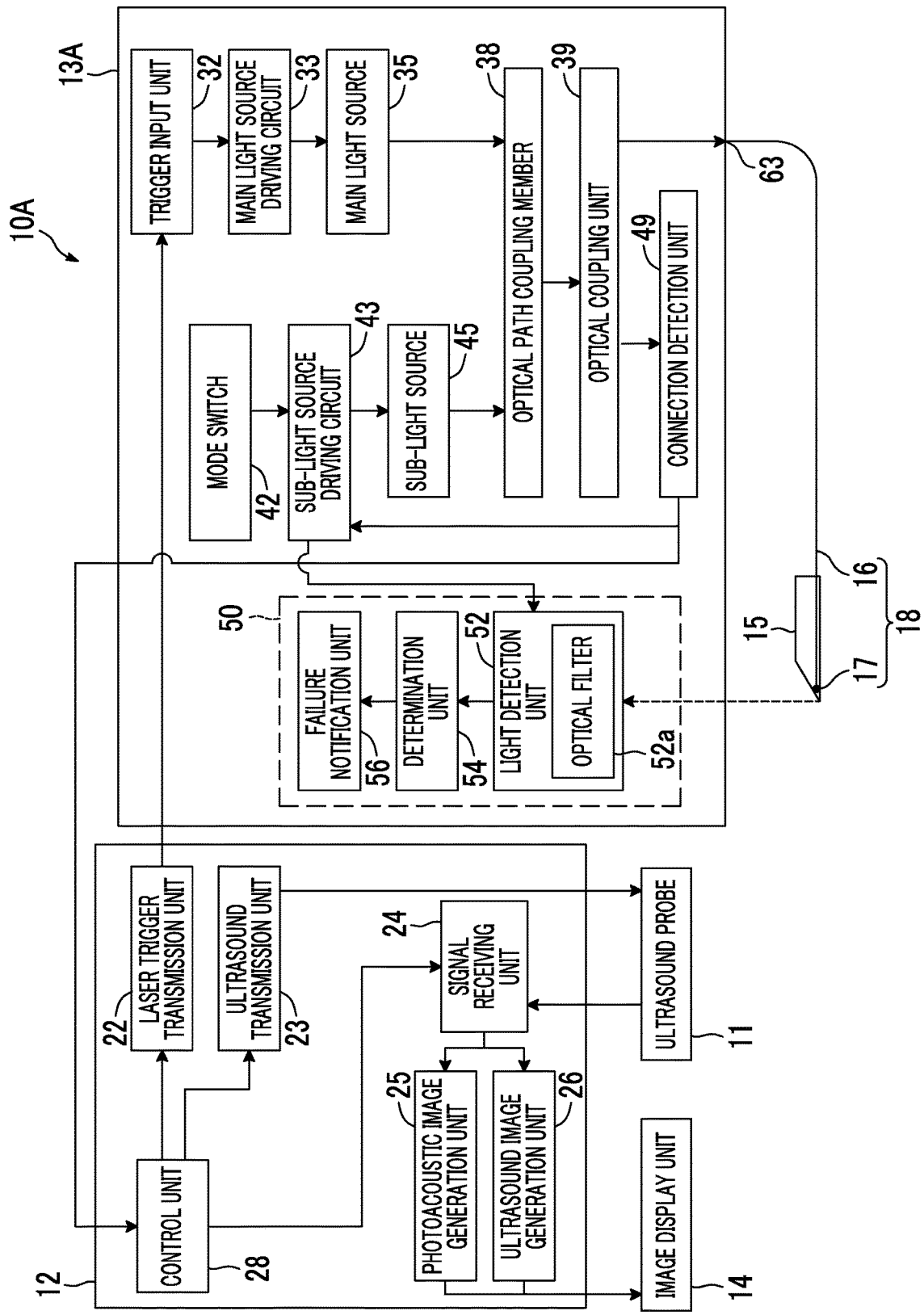
FIG. 9 is a block diagram illustrating a photoacoustic measurement apparatus according to a second embodiment of the invention.

A photoacoustic measurement apparatus 10A according to a second embodiment of the invention will be described. FIG. 9 is a block diagram illustrating the configuration of the photoacoustic measurement apparatus 10A according to the second embodiment. The same components as those in the photoacoustic measurement apparatus 10 according to the first embodiment are denoted by the same reference numerals.

In the photoacoustic measurement apparatus 10A according to this embodiment, the configuration of a laser unit 13A is partially different from that of the laser unit 13 in the photoacoustic measurement apparatus 10 according to the first embodiment. The laser unit 13A includes an optical path coupling member 38 that couples the optical paths of light emitted from the main light source 35 and the sub-light source 45 and an optical coupling unit 39 that optically couples the light guide member 16 to the main light source 35 and the sub-light source 45 through the optical path coupling member 38, instead of the optical coupling unit 36 for a main light source and the optical coupling unit 46 for a sub-light source in the laser unit 13 according to the first embodiment. In addition, the laser unit 13A includes one connection detection unit 49 instead of the main light source connection detection unit 37 and the sub-light source connection detection unit 47. The other components and the functions thereof are the same as those in the photoacoustic measurement apparatus 10 according to the first embodiment.

The optical path coupling member 38 includes a first light input unit to which light from the main light source 35 is input, a second light input unit to which light from the sub-light source 45 is input, and one light output unit that outputs the light and may be, for example, an optical fiber coupler for multiplexing. According to this configuration, since one optical coupling unit 39 is provided, it is not necessary to switch the connection of the light guide member 16 in the failure detection mode and it is possible to simply detect a failure.

The connection detection unit 49 detects the connection of the optical coupling unit 39 to the light guide member 16, similarly to the main light source connection detection unit 37 and the sub-light source connection detection unit 47, and detects the connection using, for example, a contact of a microswitch provided in a connection portion between the light guide member 16 and the optical coupling unit 39.

In this example, only in a case in which the connection detection unit 49 detects the connection, the main light source 35 and the sub-light source 45 can be driven. That is, in a case in which the connection detection unit 49 does not detect the connection, the main light source 35 and the sub-light source 45 are not driven. Therefore, it is possible to safely detect a failure of the photoacoustic wave generation unit.

In the apparatus 10A, since on optical coupling unit is provided, the mode is not capable of being switched by the switching of the connection of the light guide member 16 unlike the photoacoustic measurement apparatus 10 according to the first embodiment. The failure detection mode can be automatically set, using the detection of the connection of the light guide member 16 to the optical path coupling member 38 as a mode switch. As such, in a case in which failure detection is performed whenever the light guide member 16 is connected, a defective insert is not inserted into the subject. As a result, it is possible to reduce the redoing of a procedure or a burden on the subject. In addition, in a case in which no failure occurs after light detection is performed in the failure detection mode for a predetermined period of time, the failure detection mode may end automatically. In this case, a series of processes is smoothly performed.

Figure 10:
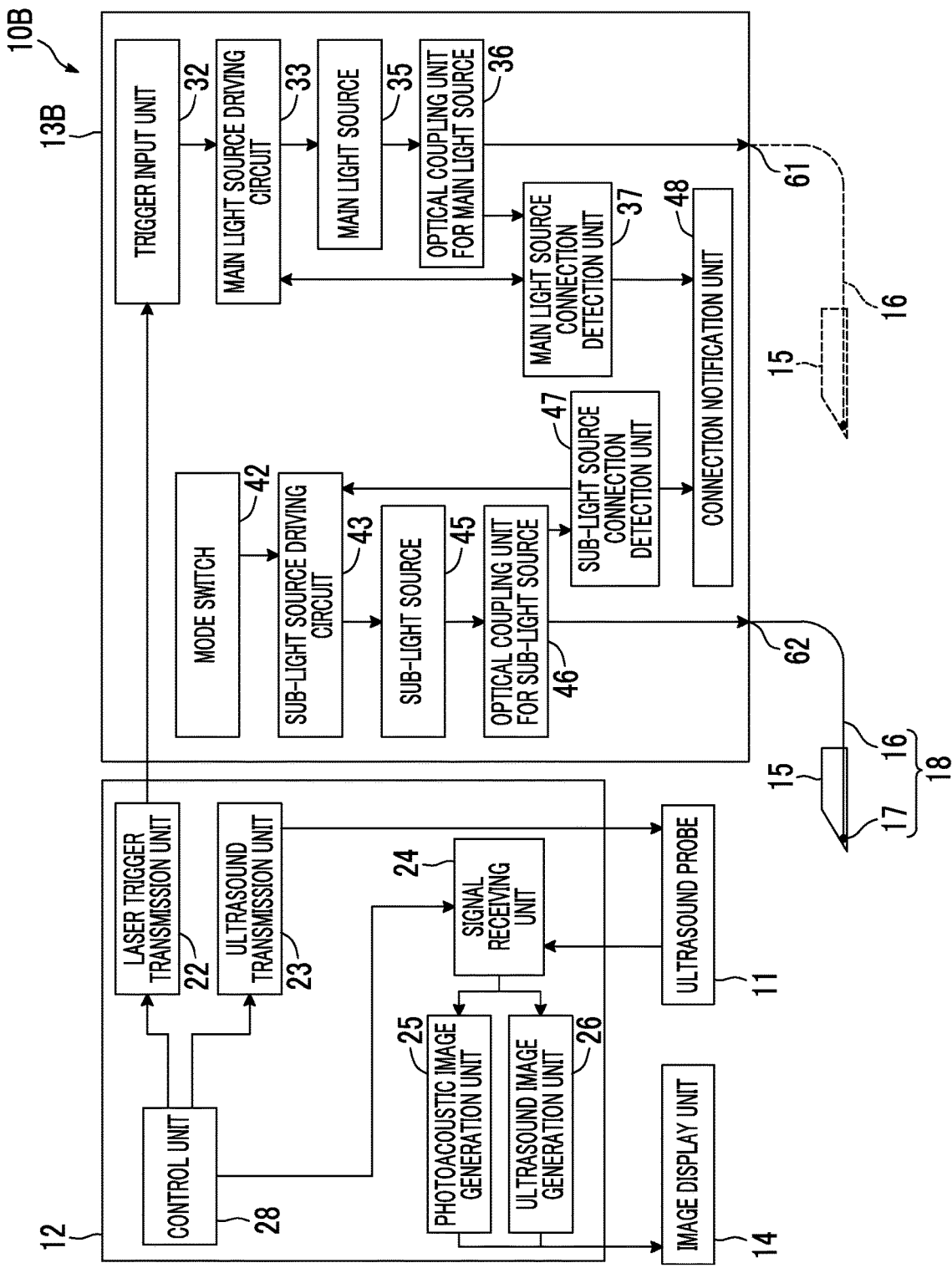
FIG. 10 is a block diagram illustrating a photoacoustic measurement apparatus according to a third embodiment of the invention.

Next, a photoacoustic measurement apparatus 10B according to a third embodiment will be described. FIG. 10 is a block diagram illustrating the photoacoustic measurement apparatus 10B according to the third embodiment.

As illustrated in FIG. 10, the photoacoustic measurement apparatus 10B according to the third embodiment differs from the photoacoustic measurement apparatus 10 according to the first embodiment in that it does not include the failure detection means 50. In this example, the failure detection means is not provided in any of the laser unit 13B, the ultrasound unit 12, and the ultrasound probe 11. The apparatus 10B is configured such that, in a case in which the main light source connection detection unit 37 detects connection, the main light source connection detection unit 37 does not transmit a connection detection signal to the control unit 28 of the ultrasound unit 12, but transmits the connection detection signal to the main light source driving circuit 33. In this case, the main light source 35 is driven first by the main light source driving circuit 33 after the connection detection signal from the main light source connection detection unit 37 is input to the main light source driving circuit 33.

The sub-light source 45 may emit light in a visible range. In this configuration, in a case in which a failure occurs in the photoacoustic wave generation unit and leakage light is generated, the user can visually recognize the leakage light.

In an optical fiber which is the light guide member, a portion that is outside the puncture needle is included in a protective member that transmits light emitted from the sub-light source 45. In a case in which breakage occurs in the optical fiber, light leaks from the broken portion. Therefore, the user can visually check damage. In addition, in a case in which the optical fiber is damaged or, for example, the deviation or detachment of the light absorption member occurs in the puncture needle, light in the visible range leaks from the leading end of the puncture needle. Therefore, the user can visually detect a failure.

As such, the photoacoustic measurement apparatus according to the invention may not necessarily include the failure detection means including the light detection unit, the determination unit, and the failure notification unit. However, in a case in which the failure detection means is provided as in the first and second embodiments, it is possible to detect the leakage light that is not detectable by the user. In addition, it is possible to perform determination based on predetermined inspection standards, which is preferable. Furthermore, it is possible to safely perform inspection even in a case in which the visible light emitted from the sub-light source is laser light, which is preferable.

In each of the above-described embodiments, the puncture needle is given as an example of the insert. However, the insert is not limited thereto. As described in JP2015-37519A, the insert may be a radio wave cauterization needle having an electrode used for radio wave cauterization, a catheter that is inserted into blood vessels, or a guide wire for the catheter inserted into blood vessels. Alternatively, the insert may be an optical fiber for a laser treatment.

In each of the above-described embodiments, the sub-light source is independent of the main light source. However, the sub-light source may include a main light source that emits infrared light and a harmonic generation element that generates harmonics of the infrared light emitted from the main light source. In this case, the main light source also functions as a portion of the sub-light source. In this case, for example, the main light source can use infrared light and the sub-light source can use visible light or near infrared light different from the infrared light used by the main light source. In a case in which the sub-light source uses near infrared light, for example, a photoelectric conversion element that detects near infrared light output from the sub-light source 45 or a combination of the filter 52a that transmits near infrared light and the photoelectric conversion element can be used as the light detection unit 52.

EXPLANATION OF REFERENCES 10, 10A, 10B: photoacoustic measurement apparatus
11: ultrasound probe (photoacoustic wave detection unit)
12: ultrasound unit
13: laser unit
14: image display unit
15: puncture needle (insert)
15a: hollow portion of puncture needle
15b: puncture needle leading end
16: light guide member
16a: leading end of light guide member
17: light absorption member
18: photoacoustic wave generation unit
19: protective member
22: laser trigger transmission unit
23: ultrasound transmission unit
24: signal receiving unit
25: photoacoustic image generation unit
26: ultrasound image generation unit
28: control unit 29: USB port
32: trigger input unit
33: main light source driving circuit
35: main light source
36: optical coupling unit for main light source
37: main light source connection detection unit
38: optical path coupling member
39: optical coupling unit
42: mode switch
43: sub-light source driving circuit
45: sub-light source
46: optical coupling unit for sub-light source
47: sub-light source connection detection unit
48: connection notification unit
49: connection detection unit
50: failure detection means
52: light detection unit
52a: optical filter
54: determination unit
56: failure notification unit
61: connection portion for normal mode
62: connection portion for failure detection mode

What is claimed is:

1. A photoacoustic measurement apparatus comprising:
    a laser unit that includes a main light source that emits pulsed laser light and a sub-light source that emits light with a wavelength different from a wavelength of the pulsed laser light;
    a light guide member that is connected to the main light source and the sub-light source so as to be switchable between the main light source and the sub-light source and guides the light which has been emitted from the main light source and the sub-light source and has been incident on a base end of the light guide member to a leading end of the light guide member;
    an insert of which at least a leading end portion is configured to be inserted into a subject and which includes at least the leading end of the light guide member and a light absorption member that is connected to the leading end of the light guide member, absorbs the pulsed laser light, and generates photoacoustic waves;
    a photoacoustic wave detection unit that detects the photoacoustic waves emitted from the leading end portion of the insert inserted into the subject,
    a photoacoustic wave generation unit including the light guide member and the light absorption member, and
    a light detection unit provided separately from the insert,
    wherein the insert is configured to be positioned over the light detection unit by a user, and
    wherein the photoacoustic measurement apparatus has a normal mode and a failure detection mode as operation modes, the failure detection mode driving the sub-light source and detecting a failure of the photoacoustic wave generation unit.

2. The photoacoustic measurement apparatus according to claim 1, further comprising:
    a protective member that includes a portion of the light guide member which is not included in the insert,
    wherein the protective member transmits the light emitted from the sub-light source.

3. The photoacoustic measurement apparatus according to claim 1, further comprising:
    an ultrasound unit that includes a photoacoustic image generation unit that generates a photoacoustic image on the basis of the detection signal of the photoacoustic waves detected by the photoacoustic wave detection unit;
    wherein the laser unit includes the light detection unit and wherein the light detection unit detects leakage light from the leading end portion of the insert; and
    the photoacoustic wave detection unit or the laser unit includes a determination unit consisting of a processor that determines the failure of the photoacoustic wave generation unit on the basis of an amount of leakage light detected by the light detection unit.

4. The photoacoustic measurement apparatus according to claim 1, further comprising:
    a main light source driving notification unit that indicates that the main light source is driven.

5. The photoacoustic measurement apparatus according to claim 1,
    wherein the laser unit further includes a main connection portion which is a connection port for connecting the light guide member in the normal mode; and
    a sub connection portion which is a connection port for connecting the light guide member in the failure detection mode.

6. The photoacoustic measurement apparatus according to claim 1,
    wherein the laser unit further includes an optical path coupling member comprising a first light input unit that is optically connected to the main light source, a second light input unit that is optically connected to the sub-light source, and one light output unit; and
    a connection portion which is a connection port for connecting the light guide member in the normal mode and the failure detection mode.

7. The photoacoustic measurement apparatus according to claim 1,
    wherein the laser unit further includes a mode switch that switches the failure detection mode between on and off.

8. The photoacoustic measurement apparatus according to claim 1,
    wherein the laser unit includes the light detection unit and wherein the light detection unit detects leakage light from the leading end portion of the insert.

9. The photoacoustic measurement apparatus according to claim 3,
    wherein the light detection unit comprises an optical filter that transmits only a wavelength range of the light emitted from the sub-light source and is provided on a light incident surface.

10. The photoacoustic measurement apparatus according to claim 3,
    wherein the determination unit determines that the failure has occurred in the photoacoustic wave generation unit in a case in which the amount of leakage light detected by the light detection unit is greater than a predetermined reference value.

11. The photoacoustic measurement apparatus according to claim 3, further comprising:
    a failure notification unit that notifies the failure in a case in which the determination unit determines that the failure has occurred in the photoacoustic wave generation unit.

12. The photoacoustic measurement apparatus according to claim 3,
    wherein the failure detection mode ends in a case in which no failure is detected in the failure detection mode for a predetermined period of time.

13. The photoacoustic measurement apparatus according to claim 5,
wherein the laser unit further includes a main microswitch provided in the main connection portion, and the main microswitch detects whether the light guide member is attached to the main connection portion.

14. The photoacoustic measurement apparatus according to claim 5,
wherein the laser unit further includes a sub microswitch provided in the sub connection portion, and the sub microswitch detects whether the light guide member is attached to the sub connection portion.

15. The photoacoustic measurement apparatus according to claim 13,
wherein the main light source is capable of being driven only in a case in which the light guide member is attached to the main connection portion.

16. The photoacoustic measurement apparatus according to claim 13,
wherein the laser unit further includes a connection notification unit that, in a case in which the main light source connection detection unit detects the connection, notifies a user of the connection.

17. The photoacoustic measurement apparatus according to claim 14,
wherein the sub-light source is capable of being driven only in a case in which the light guide member is attached to the sub connection portion.

18. The photoacoustic measurement apparatus according to claim 14,
wherein the failure detection mode starts, using the detection of the attaching of the light guide member to the sub connection portion as a mode switch.

19. The photoacoustic measurement apparatus according to claim 6,
wherein the laser unit further includes a microswitch provided in the connection portion, and the microswitch detects whether the light guide member is attached to the connection portion.

20. The photoacoustic measurement apparatus according to claim 19,
wherein the main light source or the sub-light source is capable of being driven only in a case in which the light guide member is attached to the connection portion.

21. The photoacoustic measurement apparatus according to claim 19,
wherein the failure detection mode starts, using the detection of the attaching of the light guide member to the connection portion as a mode switch.

22. The photoacoustic measurement apparatus according to claim 8,
wherein the light detection unit comprises an optical filter that transmits only a wavelength range of the light emitted from the sub-light source and is provided on a light incident surface.

\* \* \* \* \*